US00PP36552P2

(12) United States Plant Patent
Smith

(10) Patent No.: US PP36,552 P2
(45) Date of Patent: Mar. 18, 2025

(54) ***CHRYSANTHEMUM* PLANT NAMED 'CIFZ0109'**

(50) Latin Name: ***Chrysanthemum* x *morifolium***
Varietal Denomination: CIFZ0109

(71) Applicant: SYNGENTA CROP PROTECTION AG, Basel (CH)

(72) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,765

(22) Filed: Jan. 23, 2024

(51) Int. Cl.
*A01H 5/02* (2018.01)
*A01H 6/14* (2018.01)

(52) U.S. Cl.
USPC ..... Plt./287

(58) Field of Classification Search
USPC ..... Plt./287, 286
CPC ..... A01H 5/02; A01H 5/00; A01H 6/1424; A01H 6/14
See application file for complete search history.

(56) References Cited

PUBLICATIONS

Ball Seed Poppin Purple Garden Mum, retrieved on Oct. 8, 2024 at https://www.ballseed.com/PlantInfo/?phid=043100001040557, 2 pp. (Year: 2024).*
New York Botanical Gardens Chrysanthemums: Chrysanthemum Classification 2024 retrieved on Oct. 8, 2024 at https://libguides.nybg.org/c.php?g=655086&p=4597561, 8 pp. (Year: 2024).*

* cited by examiner

*Primary Examiner* — June Hwu
(74) *Attorney, Agent, or Firm* — Dale Skalla

(57) ABSTRACT

A new garden type *Chrysanthemum* plant named 'CIFZ0109' particularly distinguished by its medium to large size plant with round plant habit, a medium to small size semi-decorative flower with purple flower color, and a natural season response in mid September.

1 Drawing Sheet

Figure 1:
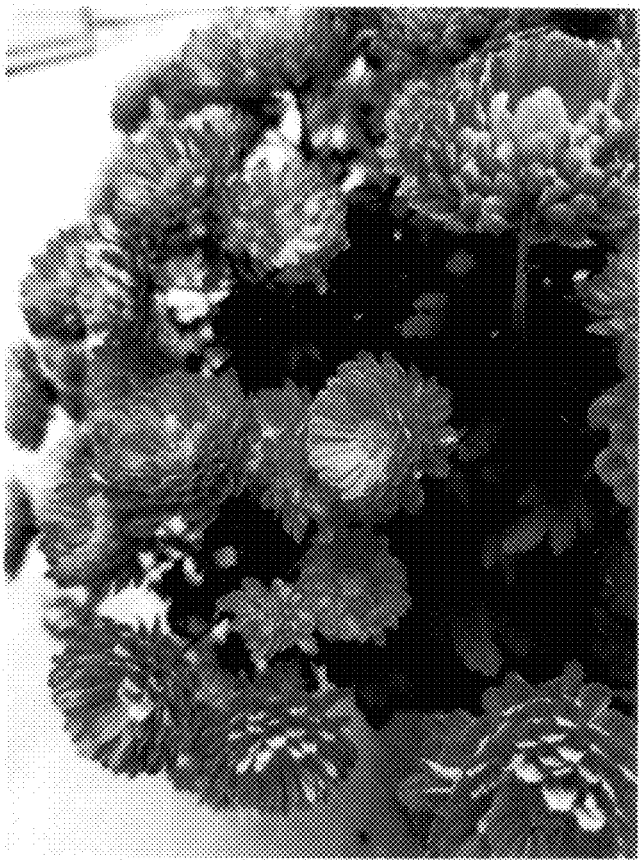

Latin name of the genus and species of the plant claimed: *Chrysanthemum* x *morifolium*.
Varietal denomination: 'CIFZ0109'.

BACKGROUND OF THE NEW PLANT

The present invention comprises a new *Chrysanthemum*, botanically known as *Chrysanthemum* x *morifolium*, and hereinafter referred to by the variety name 'CIFZ0109'.

'CIFZ0109' is a product of a planned breeding program. The new cultivar has medium to large size plant with round plant habit, a medium to small size semi-decorative flower with purple flower color, and a natural season response in mid September.

'CIFZ0109' originated from a cross made in November 2017 in Enkhuizen, The Netherlands. Seeds were sown in June 2019 in Gilroy, California and 'CIFZ0109' was selected from the resulting population on Oct. 25, 2019 in Alva, Florida.

The female parent was an unnamed, unpatented proprietary seedling '14-M332'.

TABLE 1

Characteristics of the female parent, compared to 'CIFZ0109':

| Trait | 'CIFZ0109' | '14-M332' |
|---|---|---|
| Natural response: | Similar | Similar |
| Blackcloth response: | 1/2 week slower | 1/2 week faster |
| Flower size: | Similar | Similar |
| Flower color: | Darker | Not as dark |

TABLE 1-continued

Characteristics of the female parent, compared to 'CIFZ0109':

| Trait | 'CIFZ0109' | '14-M332' |
|---|---|---|
| Plant strength: | Less brittle | More brittle |
| Flowering uniformity: | More uniform | Less uniform |
| Flower type: | Similar | Similar |
| Plant size: | Similar | Similar |

The male parent was an unnamed, unpatented proprietary seedling '14-M539'.

TABLE 2

Characteristics of the male parent, compared to 'CIFZ0109':

| Trait | 'CIFZ0109' | '14-M539' |
|---|---|---|
| Natural response: | 1.5 to 2 weeks slower | 1.5 to 2 weeks faster |
| Blackcloth response: | Similar | Similar |
| Flower size: | Similar | Similar |
| Flower color: | Darker | Lighter |
| Flower type: | Less disc florets | More disc florets |
| Plant size: | Larger | Smaller |
| Plant habit: | Similar | Similar |
| Flowering uniformity: | More uniform | Less uniform |

The first act of asexual reproduction of 'CIFZ0109' was accomplished when vegetative stem cuttings were propagated from the initial selection in January 2020 in Alva, Florida.

BRIEF SUMMARY OF INVENTION

Horticultural examination of plants grown from cuttings of the plant initiated in May 2020 and continuing thereafter, has demonstrated that the combination of characteristics as herein disclosed for 'CIFZ0109' are firmly fixed and are retained through successive generations of asexual reproduction.

'CIFZ0109' has not been observed under all possible environmental conditions. The phenotype may vary significantly with variations in environment such as temperature, light intensity and day length.

A Plant Breeder's Right for this cultivar has not yet been applied for. 'CIFZ0109' has not been made publicly available prior to the effective filing date of this application, notwithstanding any disclosure that may have been made less than one year prior to the effective filing date of this application by the inventor or another who obtained 'CIFZ0109' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawings show typical flower and foliage characteristics of 'CIFZ0109' with colors being as true as possible with an illustration of this type.

Figure 2:
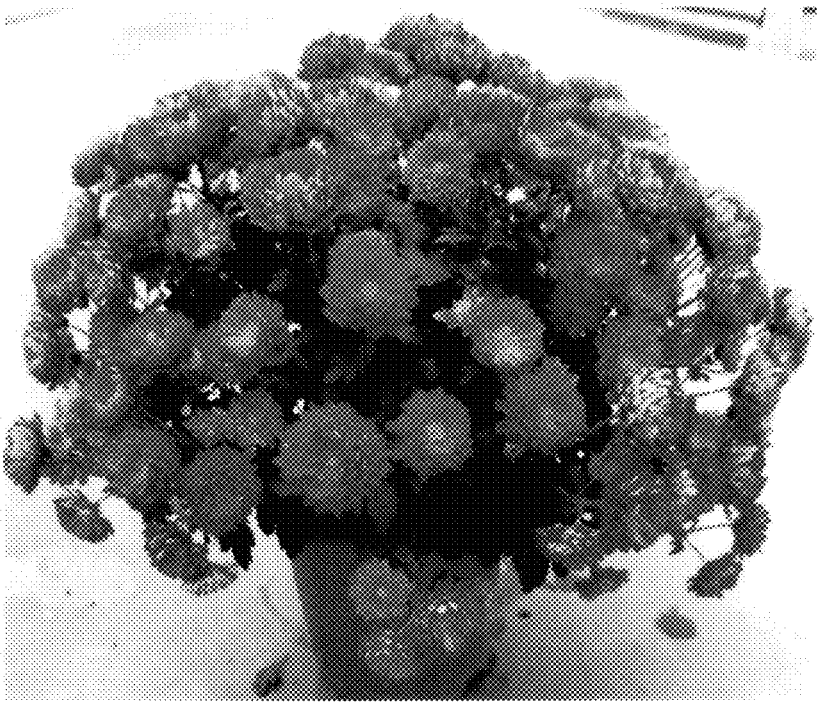

The photographic drawings show in FIG. 1 a close view of flower of the new variety and in FIG. 2 a flowering plant from an indoor trial.

The aforementioned photographs: FIG. 1, as well as FIG. 2, were taken on Sep. 12, 2023 both showing a plant from the same blackcloth indoor trial in Enkhuizen, The Netherlands.

These plants were about 13 weeks of age. One rooted cutting per pot had been planted in a 15 cm pot, not pinched in week 23, 2023 and black clothed from week 29. Plants started flowering the end of August 2023.

The measurements were taken in Enkhuizen, The Netherlands, in September 2023 on plants from the same indoor blackcloth trial.

TABLE 3

DIFFERENCES BETWEEN THE NEW VARIETY 'CIFZ0109' AND TWO MOST SIMILAR VARIETIES:

| Trait | 'CIFZ0109' | 'CIFZ0003', U.S. Plant Pat. No. PP23,762 |
|---|---|---|
| Natural response: | Longer time from bud color to open flower | Shorter time from bud color to open flower |
| Blackcloth response: | Similar | Similar |
| Flower size: | Bit larger | Bit smalller |
| Flower color: | Darker color | Lighter color |
| Flower type: | More disc florets | Less disc florets |
| Plant habit: | More mound | Rounder |
| Plant strength: | Stronger | Weaker |
| Flower longevity: | Less color fade | More color fade |
| Flowering uniformity: | Less uniform | More uniform |

TABLE 4

| Trait | 'CIFZ0109' | 'Poppin Purple', PPAF (filing number not known) |
|---|---|---|
| Natural response: | Similar but faster in the heat | Similar but slower in the heat |
| Blackcloth response: | Similar | Similar |
| Flower longevity: | 33% longer life | 33% shorter life |
| Flower size: | Smaller | Larger |
| Flower color: | Similar | Similar |
| Flower type: | More disc florets | Less disc florets |

DETAILED BOTANICAL DESCRIPTION

Color references are made to The Royal Horticultural Society Colour Chart (R.H.S.) 2001.

Plant:

*Form, growth and habit.*—Herbaceous garden-type, stems Upright and outwardly spreading, freely branching, strong and rather vigorous growth habit.

*Plant height* (*above soil*).—17 cm.

*Plant height* (*inflorescence included*).—20 cm.

*Plant width.*—34 cm.

Roots:

*Number of days to initiate roots.*—About 4 days at about 22° C.

*Number of days to produce a rooted cutting.*—14-16 days at 22° C.

*Type.*—Fine, fibrous, free branching.

Color.—RHS N155B.

Foliage:

*Arrangement.*—Alternate.

*Immature leaf, color upper surface.*—RHS 136B.

*Immature leaf, color lower surface.*—RHS 137A.

*Mature leaf, color, upper surface.*—RHS 136A.

*Mature leaf, color lower surface.*—RHS 137B.

*Length.*—5.0 cm.

*Width.*—3.5 cm.

*Shape.*—Ovate, with distinct lobes.

*Base shape.*—Shortly attenuate.

*Apex shape.*—Apiculate.

*Margin.*—5 lobed.

*Number of margin indentations.*—20-25.

*Depth of margin indentations.*—2 mm.

*Leaf length terminal lobe relative to total leaf length.*—1:6.5.

*Leaf depth lower lateral sinus.*—0.8 cm.

*Texture, upper surface.*—Bifid hairs.

*Texture, lower surface.*—Bifid hairs.

*Color of veins, upper surface.*—RHS 138B.

*Color of veins, lower surface.*—RHS 138B.

*Pattern of veining.*—Palmate.

*Petiole color.*—RHS 138B.

*Petiole length.*—1.3 cm.

*Petiole attitude.*—Moderately upwards.

*Diameter.*—0.2 cm.

*Texture.*—Bifid hairs.

*Presence of stipules.*—No.

Stem:

*Quantity of main branches per plant.*—3.

*Color of stem.*—RHS 138B.

*Length of stem.*—10-13 cm.

*Diameter.*—0.4 cm.

*Length of internodes.*—1.0-2.0 cm.

*Texture*.—Bifid hairs.
*Color of peduncle*.—RHS 146B.
*Length of peduncle*.—2.5-3.0 cm.
*Peduncle diameter*.—0.2 cm.
*Texture*.—Bifid hairs.

Inflorescence:
*Type*.—Compositae, solitary, semi-decorative inflorescences borne terminally above foliage, ligulate ray florets arranged in whorls on a capitulum giving a semi-double flower.
*Quantity of short days to flowering* (*response time*).—Approximately 7 weeks.
*Quantity of inflorescences per plant*.—About 180 with some small buds developing.
*Lastingness of individual blooms on the plant*.—About six week from first color.
*Fragrance*.—Slightly spicy.

Bud (when showing color):
*Color*.—RHS 72A.
*Length*.—0.6 cm.
*Width*.—0.5 cm.
*Shape*.—Oblate.

Immature inflorescence (at moment of opening):
*Diameter*.—1.5-2.0 cm.
*Color of ray florets, upper surface*.—RHS 72A.
*Color of ray florets, lower surface*.—RHS 78B.

Mature inflorescence:
*Diameter*.—2.5-3.0 cm.
*Depth*.—2.0 cm.
*Total diameter of disc*.—1.0 cm.
*Receptacle color*.—RHS 136A.
*Receptacle height*.—0.9 cm.
*Receptacle diameter*.—0.9 cm.
*Length of corolla tube*.—0.5 cm.

Ray florets:
*Average quantity of florets*.—110.
*Average number of rows of ray florets per flower*.—6.
*Color of florets, upper surface*.—RHS 70A.
*Color lower surface*.—RHS 77B.
*Length*.—1.1 cm.
*Width/diameter*.—0.3 cm.
*Shape*.—Oblong.
*Apex shape*.—Dentate.
*Base shape*.—Tube.
*Margin*.—Entire. Small incisions may be present at tip.
*Margin*.—Type of rolling Weakly revolute.
*Texture, upper surface*.—Papillate.
*Lower surface*.—Papillate.
*Ribs present*.—Yes.
*Number of keels*.—2.
*Profile at widest point*.—Weakly convex.
*Longitudinal axis shape*.—Weakly sinusoidal.
*Longitudinal axis curvature strength*.—Weak.
*Basal part of ray floret attitude*.—Horizontal to moderately ascending depending on the position within the inflorescence.
*Corolla tube shape*.—Circular.

Disc florets:
*Number of disc florets*.—35.
*Width*.—0.1 cm.
*Length*.—0.3 cm.
*Color*.—Base RHS 145D, top RHS 17A.

Inflorescence (at moment of senescence):
*Color of ray florets, upper surface*.—RHS 72A.
*Color of ray florets, lower surface*.—RHS 78C.

Phyllaries:
*Quantity*.—20.
*Color, upper surface*.—RHS 138B.
*Color, lower surface*.—RHS 138B.
*Length*.—0.2-0.4 cm.
*Width*.—0.1 cm.
*Shape*.—Ensiform.
*Apex shape*.—Acute.
*Base*.—Fused.
*Margins*.—Entire.
*Texture, upper surface*.—Glabrous.
*Texture, lower surface*.—Canescent.

Reproductive organs:
*Pistil*.—One.
*Length*.—0.4 cm.
*Style color*.—RHS 1C.
*Style length*.—0.4 cm.
*Stigma color*.—RHS 5D.
*Stigma shape*.—Bi-parted.
*Ovary color*.—RHS 157D.
*Ovary length*.—0.2 cm.
*Ovary width*.—0.1 cm.

Androecium:
*Stamens*.—1, found on only disc florets.
*Color of filaments*.—RHS 157C.
*Length filaments*.—0.2 cm.
*Anther color*.—RHS 2B.
*Anther length*.—0.2 cm.
*Anther shape*.—Oval to club shaped.
*Color of pollen*.—RHS 14A.
*Pollen amount*.—Moderate.
*Fertility/seed set*.—Has not been determined to date.
*Disease/pest resistance*.—Has not been determined to date.
*Hardiness*.—Has not been determined to date.

What is claimed is:

1. A new and distinct variety of *Chrysanthemum* plant named 'CIFZ0109' substantially as illustrated and described herein.

* * * * *